(12) United States Patent
Dakka et al.

(10) Patent No.: US 8,921,610 B2
(45) Date of Patent: Dec. 30, 2014

(54) OXIDATION OF ALKYLBENZENES

(75) Inventors: Jihad M. Dakka, Whitehouse Station, NJ (US); Edmund J. Mozeleski, Califon, NJ (US); Charles Morris Smith, Houston, TX (US); Christopher L. Becker, Manhattan, KS (US); Stephen Zushma, Clinton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/817,239

(22) PCT Filed: Aug. 16, 2011

(86) PCT No.: PCT/US2011/047840
§ 371 (c)(1),
(2), (4) Date: Apr. 26, 2013

(87) PCT Pub. No.: WO2012/036824
PCT Pub. Date: Mar. 22, 2012

(65) Prior Publication Data
US 2013/0211036 A1 Aug. 15, 2013

Related U.S. Application Data

(60) Provisional application No. 61/382,776, filed on Sep. 14, 2010, provisional application No. 61/491,979, filed on Jun. 1, 2011.

(51) Int. Cl.
| | | |
|---|---|---|
| C07C 409/00 | (2006.01) | |
| C07C 407/00 | (2006.01) | |
| C07C 2/74 | (2006.01) | |
| C07C 37/08 | (2006.01) | |
| C07C 45/53 | (2006.01) | |
| C07C 249/08 | (2006.01) | |
| C07C 37/11 | (2006.01) | |
| C07C 51/16 | (2006.01) | |
| C07D 223/10 | (2006.01) | |

(52) U.S. Cl.
CPC ............ *C07C 407/00* (2013.01); *C07C 2/74* (2013.01); *C07C 37/08* (2013.01); *C07C 45/53* (2013.01); *C07C 249/08* (2013.01); *C07C 37/11* (2013.01); *C07C 51/16* (2013.01); *C07D 223/10* (2013.01); *C07C 2101/14* (2013.01)
USPC ........... 568/573; 568/385; 568/558; 568/568; 568/570; 568/741

(58) Field of Classification Search
None
See application file for complete search history.

(56) References Cited

U.S. PATENT DOCUMENTS

| | | | |
|---|---|---|---|
| 3,140,243 A | | 7/1964 | Feder et al. |
| 3,322,651 A | | 5/1967 | Nielsen |
| 3,442,958 A | | 5/1969 | Choo |
| 3,523,977 A | * | 8/1970 | Reni et al. ............... 568/574 |
| 3,692,845 A | | 9/1972 | Cheema et al. |
| 3,821,314 A | | 6/1974 | Arkell et al. |
| 3,933,916 A | | 1/1976 | Lejeune et al. |
| 3,959,381 A | | 5/1976 | Arkell et al. |
| 4,021,490 A | | 5/1977 | Hudson |
| 4,092,360 A | | 5/1978 | Van Peppen et al. |

(Continued)

FOREIGN PATENT DOCUMENTS

| | | |
|---|---|---|
| EP | 0 492 807 | 7/1992 |
| EP | 1 074 536 | 2/2001 |

(Continued)

OTHER PUBLICATIONS

Aoki et al., "*One-pot synthesis of phenol and cyclohexanone from cyclohexylbenzene catalyzed by N-hydroxyphthalimide (NHPI),*" Tetrahedron, 2005, vol. 61, pp. 5219-5222.

(Continued)

*Primary Examiner* — Sudhakar Katakam
(74) *Attorney, Agent, or Firm* — Stephen A. Baehl; Siwen Chen

(57) ABSTRACT

A process for oxidizing a composition comprising contacting an alkylbenzene of the general formula (I):

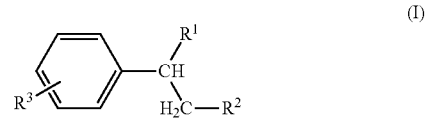

where $R^1$ and $R^2$ each independently represents hydrogen or an alkyl group having from 1 to 4 carbon atoms, wherein $R^1$ and $R^2$ may be joined to form a cyclic group having from 4 to 10 carbon atoms, the cyclic group being optionally substituted, and $R^3$ represents hydrogen, one or more alkyl groups having from 1 to 4 carbon atoms or a cyclohexyl group; and (ii) about 0.05 wt % to about 5 wt % of phenol, with oxygen in the presence of a catalyst containing a cyclic imide having the general formula (II):

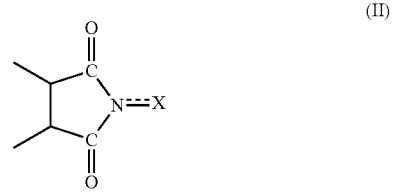

wherein X represents an oxygen atom, a hydroxyl group, or an acyloxy group under conditions effective to convert at least a portion of the alkylbenzene to a hydroperoxide.

23 Claims, 2 Drawing Sheets

(56) References Cited

U.S. PATENT DOCUMENTS

| | | | |
|---|---|---|---|
| 4,230,638 A | 10/1980 | Murtha | |
| 4,262,151 A | 4/1981 | Pujado | |
| 4,358,618 A | 11/1982 | Sifniades et al. | |
| 4,480,141 A | 10/1984 | Drake | |
| 4,482,757 A | 11/1984 | Drake | |
| 4,487,970 A | 12/1984 | Drake | |
| 4,487,974 A * | 12/1984 | Sanderson | 568/570 |
| 4,490,565 A | 12/1984 | Chang et al. | |
| 4,490,566 A | 12/1984 | Chang et al. | |
| 4,870,217 A | 9/1989 | Knifton | |
| 4,898,995 A | 2/1990 | Knifton et al. | |
| 5,064,507 A | 11/1991 | O'Donnell et al. | |
| 5,066,373 A | 11/1991 | Levy et al. | |
| 5,254,751 A | 10/1993 | Zakoshansky | |
| 5,283,376 A | 2/1994 | Dyckman et al. | |
| 6,037,513 A | 3/2000 | Chang et al. | |
| 6,169,215 B1 | 1/2001 | Levin et al. | |
| 6,201,157 B1 | 3/2001 | Keenan | |
| 6,284,927 B1 | 9/2001 | Druliner et al. | |
| 6,388,144 B1 | 5/2002 | Wijesekera et al. | |
| 6,720,462 B2 | 4/2004 | Kuhnle et al. | |
| 6,852,893 B2 | 2/2005 | Kuhnle et al. | |
| 6,965,056 B1 | 11/2005 | Taggart, II et al. | |
| 7,002,048 B2 | 2/2006 | Wijesekera et al. | |
| 7,199,271 B2 | 4/2007 | Fodor | |
| 7,205,442 B2 | 4/2007 | Payne | |
| 7,799,956 B2 | 9/2010 | Cheng et al. | |
| 2002/0169331 A1 | 11/2002 | Miura et al. | |
| 2003/0083527 A1 | 5/2003 | Kuhnle et al. | |
| 2004/0162446 A1 | 8/2004 | Black | |
| 2004/0236152 A1 | 11/2004 | Black et al. | |
| 2007/0265476 A1* | 11/2007 | Dakka et al. | 568/385 |
| 2011/0037022 A1 | 2/2011 | Dakka et al. | |
| 2011/0190546 A1 | 8/2011 | Dakka et al. | |

FOREIGN PATENT DOCUMENTS

| | | |
|---|---|---|
| EP | 1 728 779 | 12/2006 |
| GB | 681613 | 10/1952 |
| JP | 2007-099745 | 12/2005 |
| JP | 2007-099746 | 12/2005 |
| WO | 2006/015826 | 2/2006 |
| WO | 2008/128638 | 10/2008 |
| WO | 2009/025939 | 2/2009 |
| WO | 2009/058527 | 5/2009 |
| WO | 2009/058531 | 5/2009 |
| WO | 2009/128984 | 10/2009 |
| WO | 2010/042261 | 4/2010 |
| WO | 2010/098916 | 9/2010 |
| WO | 2011/001244 | 1/2011 |
| WO | 2011/031374 | 3/2011 |

OTHER PUBLICATIONS

Ishii et al., "*Recent progress in aerobic oxidation of hydrocarbons by N-hydroxyimides*," Catalysis Today, 2006, vol. 117, pp. 105-113.

Knifton et al., "*Phenol/acetone cogeneration via solid acid catalysis*," Applied Catalysis A: General, 1997, vol. 161, pp. 199-211.

Koltunov et al., "*Efficient cleavage of cumene hydroperoxide over HUSY zeolites: The role of Bronsted acidity*," Applied Catalysis A: General, 2008, vol. 336, pp. 29-34.

Maksimov et al., "$WO_3/MO_2$ (*M=Zr, Sn, Ti*) *Heterogeneous Acid Catalysts: Synthesis, Study, and Use in Cumene Hydroperoxide Decomposition*," Kinetics and Catalysis, 2006, vol. 47, No. 4, pp. 564-571.

Meier et al., Atlas of Zeolites Structure Types, 2001—Abstract only.

Schmidt et al., "*New Developments in the Sunoco/UOP Phenol Technology*," presented at the AIChE Spring Meeting (Apr. 2004), New Orleans, LA.

Schmidt, "*Industrial catalytic processes—phenol production*," Applied Catalysis A: General, 2005, vol. 280, pp. 89-103.

Selvin et al., "*Catalytic decomposition of cumene hydroperoxide into phenol and acetone*," Applied Catalysis A: General, 2001, vol. 219, pp. 125-129.

Zakoshansky, "*Acid-Catalytic Cumene Hydroperoxide Cleavage Process in Boiling Acetone Medium*," presented at the AIChE Spring Meeting (Mar. 2002), New Orleans, LA.

Wang et al., U.S. Appl. No. 61/476,893, "*Process for Producing Phenol*," filed Apr. 19, 2011.

* cited by examiner

OXIDATION OF ALKYLBENZENES

PRIORITY CLAIM

This application is a National Stage Application of International Application No. PCT/US2011/047840 filed Aug. 16, 2011, which claims priority to and the benefit of U.S. Provisional Application Ser. Nos. 61/491,979 filed Jun. 1, 2011 and Ser. No. 61/382,776 filed Sep. 14, 2010, both of which are incorporated herein by reference in their entirety.

CROSS REFERENCE TO RELATED APPLICATIONS

This application is related to U.S. application Ser. No. 12/678,419; and U.S. Prov. Nos. 61/424,229; and 61/468,290.

FIELD

The present invention relates to a process for oxidizing alkylbenzenes and, in particular, to a process for oxidizing alkylbenzenes and then cleaving the resultant hydroperoxide to produce phenol and a ketone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process involving alkylation of benzene with propylene to produce cumene, followed by oxidation of the cumene to cumene hydroperoxide and then cleavage of the hydroperoxide to produce equimolar amounts of phenol and acetone.

Another route involves alkylation of benzene with a $C_4$ alkylating agent, such as a linear butene, to produce sec-butyl benzene, followed by oxidation of the sec-butyl benzene to corresponding hydroperoxide and then cleavage of the hydroperoxide to produce equimolar amounts of phenol and methyl ethyl ketone. An example of such a process, in which the alkylation is conducted in the presence of a catalyst comprising a molecular sieve of the MCM-22 family, is described in U.S. Pat. No. 7,799,956.

Another possible alternative to the conventional Hock process involves the catalytic hydroalkylation of benzene to produce cyclohexylbenzene, followed by the oxidation of the cyclohexylbenzene to cyclohexylbenzene hydroperoxide, which is then cleaved to produce phenol and cyclohexanone in substantially equimolar amounts. Such a process is described in, for example, U.S. Pat. No. 6,037,513, in which the hydroalkylation catalyst is a bifunctional catalyst comprising at least one hydrogenation metal and a molecular sieve of the MCM-22 family.

However, one problem in producing phenol via sec-butyl benzene or cyclohexylbenzene is that the oxidation of these higher alkylbenzenes is considerably more difficult than that of cumene. Thus, whereas cumene oxidation is normally conducted in the absence of a catalyst, oxidation of sec-butyl benzene and cyclohexylbenzene typically requires the presence of a cyclic imide catalyst, such as N-hydroxyphthalimide (NHPI), to provide commercially acceptable levels of conversion. Thus, the oxidation proceeds via a free radical chain mechanism and the NHPI increases radical initiation and propagation rates and strongly reduces radical termination rates, thereby improving conversion and selectivity. However, even using NHPI as a catalyst, the selectivity to the desired hydroperoxide decreases with increasing conversion. Thus, the product of the oxidation step typically contains large amounts (of the order of 80 wt %) of unreacted alkylbenzene which must be recycled to ensure acceptable process economics.

The oxidation process also produces a number of undesirable impurities, including certain organic acid species. In addition to hydrolyzing the NHPI, these acid species are known to catalyze cleavage of alkylbenzene hydroperoxides to produce phenol. Although phenol is the desired end-product, its presence during the oxidation process is highly deleterious since, abstraction of a hydrogen atom from phenol, produces the phenoxide radical, which is a stable species having a long lifetime and a slow propagation reaction rate. Thus, phenol inhibits the free radical reactions necessary for the oxidation process to proceed to the hydroperoxide. In the oxidation of cumene in the absence of NHPI, cleavage of the hydroperoxide is prevented by the addition of a base to neutralize any acidic species. However, in the NHPI catalyzed oxidation of alkylbenzenes, addition of base cannot be considered because the base will react with the NHPI and neutralize the O—H bond, which is responsible for the free radical initiation and propagation reactions.

Thus, current methods of oxidizing alkylbenzenes that employ cyclic imide catalysts, such as NHPI, require expensive treatment of the unreacted alkylbenzene to reduce the level of phenol in their recycle streams to very low ppm values. Surprisingly, however, it has now been shown that NHPI will react with phenol under the conditions present in the oxidation reactor to produce an ether species, which has little or no inhibiting effect on the oxidation reaction. As a result it has been found that significantly higher levels of phenol than previously expected can be tolerated in the feed to oxidation reaction, thereby allowing recycle of unreacted alkylbenzene with little or reduced pre-treatment to remove phenol.

U.S. Patent Application Publication No 2011/0037022 discloses a process for producing phenol and/or cyclohexanone by (a) contacting benzene and hydrogen with a first catalyst under hydroalkylation conditions to produce a first effluent stream comprising cyclohexylbenzene, cyclohexane, and unreacted benzene; (b) supplying at least part of the first effluent stream to a first separation system to divide the first effluent stream part into a cyclohexylbenzene-rich stream, a $C_6$ product stream comprising cyclohexane and benzene; (c) contacting at least part of the $C_6$ product stream with a second catalyst under dehydrogenation conditions to convert at least part of the cyclohexane to benzene and produce a second effluent stream comprising benzene and hydrogen; (d) recycling at least part of the second effluent stream to the contacting (a); (e) contacting at least part of the cyclohexylbenzene-rich stream with an oxygen-containing gas in the presence of a third catalyst under oxidation conditions to oxidize the cyclohexylbenzene in the cyclohexylbenzene-rich stream to produce cyclohexylbenzene hydroperoxide; and (f) cleaving cyclohexylbenzene hydroperoxide from (e) to produce phenol and cyclohexanone. Cyclohexylbenzene which is unconverted in the oxidation step (e) is recovered after the cleavage step (f), and is recycled to the oxidation reaction, but according to paragraph [0086], only after the oxidation effluent is treated to remove acids, such as organic acids produced as byproducts of the oxidation reaction and phenolic acids present in the cyclohexylbenzene recycle stream(s).

SUMMARY

Accordingly, the invention resides in one aspect, in a process for oxidizing an alkylbenzene, the process comprising:

(a) supplying a composition comprising (i) an alkylbenzene of the general formula (I):

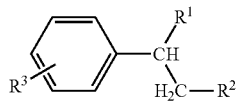

where $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, the cyclic group being optionally substituted, and $R^3$ represents hydrogen, one or more alkyl groups having from 1 to 4 carbon atoms or a cyclohexyl group and (ii) about 0.05 wt % to about 5.0 wt % of phenol, the wt % based upon total weight of the composition; and (b) contacting the composition with oxygen in the presence of a catalyst containing a cyclic imide having the general formula (II):

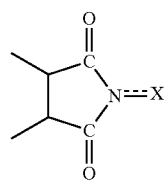

wherein X represents an oxygen atom, a hydroxyl group, or an acyloxy group and wherein the contacting step (b) is conducted under conditions effective to convert at least a portion of the alkylbenzene to a hydroperoxide.

Conveniently, the composition comprises from about 0.1 wt % to about 1 wt %, such as about 0.15 wt % to about 0.5 wt %, of phenol based upon total weight of the composition.

Conveniently, the alkylbenzene is selected from cumene, sec-butylbenzene, cyclohexylbenzene and mixtures thereof.

Conveniently, the cyclic imide has the general formula (III):

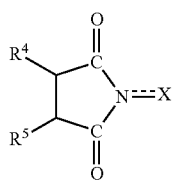

wherein X represents an oxygen atom, a hydroxyl group, or an acyloxy group and $R^4$ and $R^5$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^4$ and $R^5$ may be bound together to form a double bond or an aromatic- or non-aromatic ring.

In one embodiment, the cyclic imide comprises N-hydroxyphthalimide.

Generally, the cyclic imide is added to the composition in an amount between 0.05 wt % and 5 wt % of the composition.

In one embodiment, the method further comprises:

(c) cleaving at least part of the alkylbenzene hydroperoxide produced by the contacting step (b) to produce phenol.

Conveniently, at least part of the phenol present in the composition supplied to the contacting step (b) is contained in an unreacted alkylbenzene stream recycled from the contacting step (b) and/or the cleaving step (c).

In a further aspect, the invention resides in a process for producing phenol and/or cyclohexanone, the process comprising:

(a) contacting benzene and hydrogen under hydroalkylation conditions to produce cyclohexylbenzene;

(b) supplying a feed comprising (i) at least part of the cyclohexylbenzene from the contacting step (a) and 0.05 wt % to 5 wt % of phenol based upon total weight of the feed to at least one oxidation reaction zone;

(c) contacting the feed in the at least one oxidation reaction zone with an oxygen-containing gas in the presence of a catalyst containing a cyclic imide having the general formula (II)

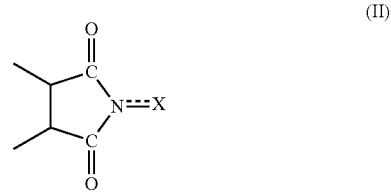

wherein X represents an oxygen atom, a hydroxyl group, or an acyloxy group and wherein the contacting step (c) is conducted under conditions effective to convert at least a portion of the cyclohexylbenzene to cyclohexylbenzene hydroperoxide and produce an oxidation effluent stream comprising cyclohexylbenzene hydroperoxide and unreacted cyclohexylbenzene;

(d) cleaving at least a portion of the cyclohexylbenzene hydroperoxide in at least one cleavage reaction zone to produce a cleavage effluent stream comprising phenol, cyclohexanone and unreacted cyclohexylbenzene; and (e) providing a recycle stream comprising unreacted cyclohexylbenzene and at least 0.05 wt % phenol from the oxidation effluent stream and/or the cleavage effluent stream to the at least one oxidation reaction zone.

DETAILED DESCRIPTION OF THE EMBODIMENTS

Figure 1:
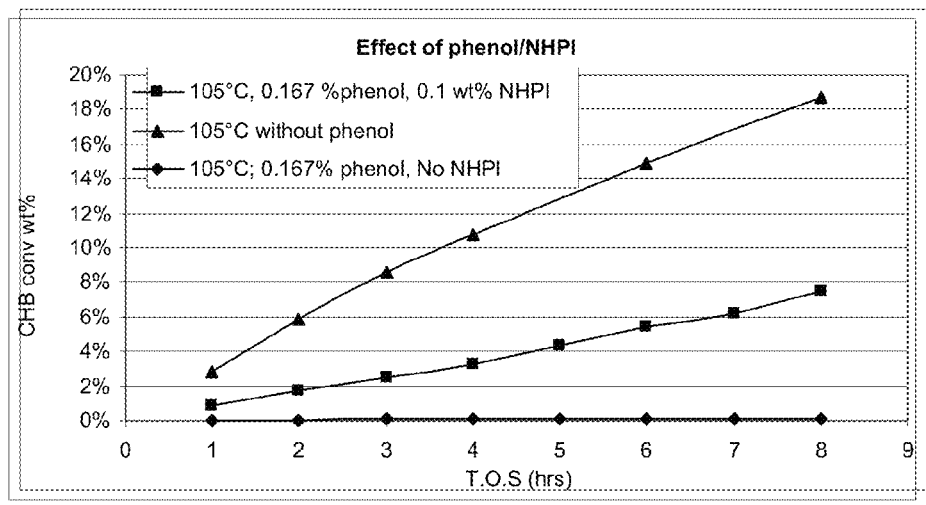
FIG. 1 is a graph comparing the cyclohexylbenzene conversion against time on stream for the oxidation of cyclohexylbenzene in the presence of N-hydroxyphthalimide (NHPI) according to Example 1, the oxidation of cyclohexylbenzene in the presence of 0.167 wt % phenol according to Example 2 and the oxidation of cyclohexylbenzene in the presence of 0.167 wt % phenol and N-hydroxyphthalimide (NHPI) according to Example 3, all being conducted at 105° C.

Described herein is a process for oxidizing an alkylbenzene of the general formula (I):

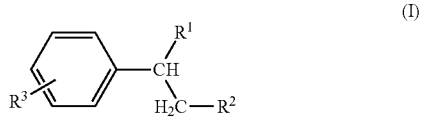

where $R^1$ and $R^2$ each independently represents hydrogen or an alkyl group having from 1 to 4 carbon atoms, provided that $R^1$ and $R^2$ may be joined to form a cyclic group having from 4 to 10 carbon atoms, the cyclic group being optionally substituted, and $R^3$ represents hydrogen, one or more alkyl groups having from 1 to 4 carbon atoms or a cyclohexyl group. Examples of suitable alkylbenzenes include cumene, sec-butylbenzene, cyclohexylbenzene and mixtures thereof, with cyclohexylbenzene being preferred.

The oxidation process is conducted in the presence of a cyclic imide catalyst, such as N-hydroxyphthalimide, and counter-intuitively in the presence of about 0.05 wt % to about 5 wt % of phenol, typically present as an impurity in an unreacted alkylbenzene stream recycled from the oxidation step and/or a downstream cleavage step. Thus, based on experience with the conventional Hock process, in which benzene is alkylated to cumene and the cumene undergoes autoxidation and cleavage to phenol, it has been assumed that the presence of phenol in the oxidation step should be avoided since phenol inhibits the free radical reactions necessary for the oxidation process to proceed to the hydroperoxide. However, it has now been found that when the oxidation is conducted in the presence of a cyclic imide catalyst, such as N-hydroxyphthalimide, the catalyst is effective in removing small quantities of phenol by producing an ether species, which has little or no inhibiting effect on the oxidation reaction. As a result, recycled alkylbenzene streams can contain considerably larger concentrations of phenol than had previously been thought, thereby alleviating the need for costly purification/treatment of the recycle streams.

In one preferred embodiment, the present oxidation process forms part of an integrated process for producing phenol and cyclohexanone from benzene, in which the benzene is converted to cyclohexylbenzene, the cyclohexylbenzene is then oxidized to cyclohexylbenzene hydroperoxide and the cyclohexylbenzene hydroperoxide is cleaved to produce phenol and cyclohexanone. The present process will therefore be more particularly described with reference to this preferred embodiment.

Production of the Cyclohexylbenzene

An initial step in the present process may involve the production of cyclohexylbenzene by reacting benzene with cyclohexene in the presence of a catalyst having an alkylation function and under conditions to promote the following reaction:

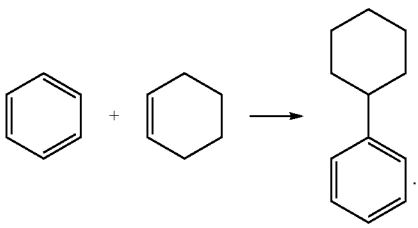 [SMILES: c1ccccc1 ; C1=CCCCC1 ; c1ccc(C2CCCCC2)cc1]

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

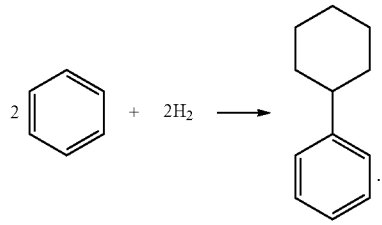 [SMILES: c1ccccc1 ; c1ccc(C2CCCCC2)cc1]

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, of water. In addition, the total feed typically contains less than 100 ppm, such as less than 30 ppm, for example less than 3 ppm, sulfur and less than 10 ppm, such as less than 1 ppm, for example less than 0.1 ppm, of nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Treatment of the Cyclohexylbenzene Product

Although the hydroalkylation reaction using an MCM-22 family zeolite catalyst is highly selective towards cyclohexylbenzene, the liquid effluent from the hydroalkylation reaction may contain significant quantities of unreacted benzene and certain by-products in addition to the desired cyclohexylbenzene. One of the major by-products are polycyclohexylbenzenes (di- and tricyclohexylbenzene), which typically comprise up to 20 wt % of the conversion products. Thus, for the overall process to be economically feasible, it is necessary to convert these polycyclohexylbenzenes into additional useful cyclohexylbenzene product. This can be achieved by transalkylation or dealkylation, but initially it is necessary to separate the polycyclohexylbenzenes from the reaction product.

Separation of the polycyclohexylbenzenes is conveniently achieved by supplying at least a portion of the reaction product to a fractionation device, normally a fractionation column, to separate the reaction product into at least a first fraction rich in cyclohexylbenzene and a second fraction rich in polycyclohexylbenzenes. In addition, to allow the separation to be effected at or near atmospheric pressure (about 100 kPa to about 300 kPa) and at relatively low temperatures, at least one $C_4$ to $C_6$ hydrocarbon in the vapor phase is supplied separately to the fractionation device, normally at or adjacent the base of the fractionation column. Although any $C_4$ to $C_6$ hydrocarbon vapor can be used, benzene vapor is particularly useful since, for example, the hydroalkylation reaction effluent contains significant quantities (typically up to 60 wt %) of unreacted benzene.

Conveniently, the $C_4$ to $C_6$ hydrocarbon vapor is supplied to the fractionation device at a temperature of about 190° C. to about 300° C. More particularly, where steam is used to heat and vaporize the $C_4$ to $C_6$ hydrocarbon, the temperature of the $C_4$ to $C_6$ hydrocarbon vapor supplied to the fractionation device is between about 190° C. and about 241° C. Generally, the ratio of the weight of the $C_4$ to $C_6$ hydrocarbon vapor supplied to the fractionation device to the weight of the reaction product supplied to the fractionation device is from about 0.05:1 to about 2:1, such as from about 0.1:1 to about 1:1, for example about 0.5:1.

In one embodiment of the present process, after separation from the hydroalkylation reaction effluent, the polycyclohexylbenzenes are mixed with benzene and transalkylated to produce additional monocyclohexylbenzene. Transalkylation is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 to about 10 $hr^{-1}$ on total feed, and a benzene/dicyclohexylbenzene weight ratio about of 1:1 to about 5:1.

In another embodiment of the present process, conversion of the polycyclohexylbenzenes to additional monocyclohexylbenzene is effected by dealkylation. Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa, gauge) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia and mixtures thereof. Generally, the acid catalyst includes at least one aluminosilicate, aluminophosphate or silicoaluminphosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 to 50 $hr^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

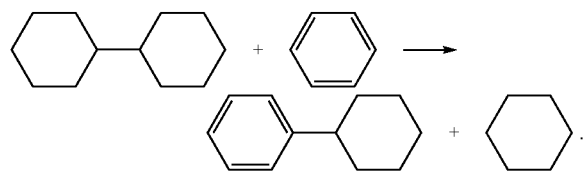

The catalytic treatment can be conducted on the direct product of the hydroalkylation reaction or after distillation of the hydroalkylation reaction product to separate the $C_6$ and/or the heavies fraction.

The cyclohexylbenzene-rich stream separated from the hydroalkylation reaction product is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air.

The oxidation is conducted in the presence of a catalyst and especially an N-hydroxy substituted cyclic imide catalyst as described in U.S. Pat. No. 6,720,462, incorporated herein by reference. Suitable catalysts comprise an imide group having the following formula II:

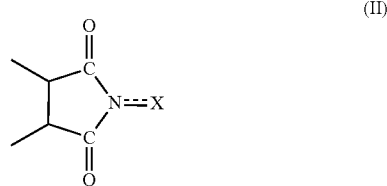

wherein X represents an oxygen atom, a hydroxyl group, or an acyloxy group.

Generally, the cyclic imide catalyst obeys the general formula III:

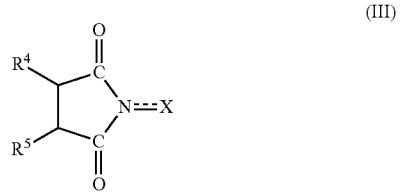

wherein X represents an oxygen atom, a hydroxyl group, or an acyloxy group and $R^4$ and $R^5$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^4$ and $R^5$ may be bound together to form a double bond or an aromatic- or non-aromatic ring.

In one practical embodiment, the cyclic imide catalyst comprises N-hydroxyphthalimide or N,N',N''-trihydroxyisocyanuric acid.

The cyclic imide oxidation catalyst can be used either alone or in conjunction with a free radical initiator, and further can be used as a liquid-phase, homogeneous catalyst or can be supported on a solid carrier to provide a heterogeneous catalyst. Typically, the cyclic imide catalyst is employed in an amount between 0.0001 wt % to 15 wt %, such as between 0.001 wt % to 5 wt %, of the cyclohexylbenzene.

The oxidation reaction may be conducted in a single reaction zone or in a plurality of reaction zones connected in series, with each reaction zone conducting a portion of the oxidation reaction. Where multiple reaction zones are employed, they may be part of a single reactor or two or more of the reaction zones may be located in different reactors. The oxidation conditions are arranged to be the same or different in each reaction zone.

As will be discussed in the following section, only part of the cyclohexylbenzene in the oxidation feed is converted to cyclohexylbenzene hydroperoxide in the oxidation reaction. Thus, the oxidation reaction effluent necessarily contains significant quantities, generally of the order of 80 wt %, of unreacted cyclohexylbenzene, which must be recycled to the oxidation step, either directly or following the cleavage reaction. However, the oxidation process also produces a number of undesirable impurities, including certain organic acid species, which catalyze cleavage of cyclohexylbenzene hydroperoxide to phenol. Thus, whether separated from the oxidation reaction effluent or the cleavage reaction effluent, the unreacted cyclohexylbenzene inevitably contains phenol, typically in amounts of 0.001 wt % to 0.5 wt %. In the past, it was believed to be necessary to subject these unreacted recycle streams to expensive purification procedures to reduce the phenol level to very low ppm levels so as to avoid inhibition of the oxidation reaction. However, it has now been found that cyclic imides, such as NHPI, react with phenol to produce ether species, which have little or no inhibiting effect on the oxidation reaction. Thus, provided the level of phenol in the oxidation feed is kept at about 0.05 wt % to about 5.0 wt %, such as about 0.1 wt % to about 1 wt %, for example about 0.15 wt % to about 0.5 wt %, by weight of the overall feed, the oxidation proceeds without significant loss of activity or selectivity. This allows treatment of the recycle cyclohexylbenzene to remove the phenol by-product to be either avoided or at least significantly simplified.

In various embodiments, the NHPI reacts away at least 5% of the phenol, or at least 10%, or at least 20%, or at least 35%, or at least 50% of the phenol present.

Purification of the Oxidation Product

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939.

Hydroperoxide Cleavage

Another step in the conversion of the cyclohexylbenzene into phenol and cyclohexanone involves the acid-catalyzed cleavage of the cyclohexylbenzene hydroperoxide recovered from the oxidation reaction effluent.

Generally, the acid catalyst used in the cleavage reaction is at least partially soluble in the cleavage reaction mixture and at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to and to no greater than 3000 wppm, or at least 150 wppm to and no greater than 2000 wppm of the acid catalyst, or at least 300 wppm and no greater than 1500 wppm of the acid catalyst, based upon total weight of the cleavage reaction mixture.

In one embodiment, the cleavage reaction mixture contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less, such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

Suitable cleavage conditions include a temperature of at least 20° C. and no greater than 200° C., or at least 40° C. and no greater than 120° C., and a pressure of at least 1 and no greater than 370 psig (at least 7 and no greater than 2,550 kPa, gauge), or at least 14.5 and no greater than 145 psig (at least 100 and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction are phenol and cyclohexanone, each of which generally comprises about 40 wt % to about 60 wt %, or about 45 wt % to about 55 wt % of the cleavage reaction product, such wt % based on the weight of the cleavage reaction product exclusive of unreacted cyclohexylbenzene and acid catalyst.

The cleavage reaction product also typically contains unreacted acid catalyst and hence at least a portion of the cleavage reaction product may be neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay such as limestone, dolomite, magnesite, sepiolite and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium and radium; an oxide of Group III of the Periodic Table of Elements treated with a metal selected from lithium, potassium, sodium, rubidium and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines and alkanolamines. In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on the least a portion of the treated cleavage reaction product that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 psig to about 500 psig (5 kPa to 3450 kPa, gauge), or about 10 psig to 200 psig (70 kPa to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which can be purified and separated by methods well known in the art.

The invention will now be more particularly described with reference to the following non-limiting Examples and the accompanying drawings.

EXAMPLE 1

Oxidation of Cyclohexylbenzene (CHB) Using NHPI Catalyst 150 g of cyclohexylbenzene from TCI America and 0.16 g NHPI from TCI were weighed into a Parr reactor fitted with a stirrer, thermocouple, gas inlet, sampling port and a condenser containing a Dean-Stark trap for water removal. The reactor contents were stirred at 1000 rpm and sparged with nitrogen at a flow rate of 250 cc/minute for 5 minutes. The reactor, while maintained under a nitrogen sparge, was then heated to 105° C. When the reaction temperature was reached, the gas was switched from nitrogen to air and the reactor was sparged with air at 250 cc/minute. Samples were taken and analyzed by gas chromatography. At the end of the reaction, the gas was switched back to nitrogen and the heat was turned off.

EXAMPLE 2

Oxidation of CHB in the Presence of 0.167 Wt % Phenol 150 g of cyclohexylbenzene and 0.2505 g phenol from TCI America were weighed into a Parr reactor fitted with a stirrer, thermocouple, gas inlet, sampling port and a condenser containing a Dean-Stark trap for water removal. The reactor contents were stirred at 1000 rpm and sparged with nitrogen at a flow rate of 250 cc/minute for 5 minutes. The reactor, while maintained under a nitrogen sparge, was then heated to 105° C. When the reaction temperature was reached, the gas was switched from nitrogen to air and the reactor was sparged with air at 250 cc/minute. Samples were taken and analyzed by gas chromatography. At the end of the reaction, the gas was switched back to nitrogen and the heat was turned off.

EXAMPLE 3

Oxidation of CHB in the Presence of 0.167 Wt % Phenol and NHPI Catalyst 150 g of cyclohexylbenzene and 0.2505 g phenol from TCI America and 0.16 g NHPI from TCI were weighed into a Parr reactor fitted with a stirrer, thermocouple, gas inlet, sampling port and a condenser containing a Dean-Stark trap for water removal. The reactor contents were stirred at 1000 rpm and sparged with nitrogen at a flow rate of 250 cc/minute for 5 minutes. The reactor, while maintained under a nitrogen sparge, was then heated to 105° C. When the reaction temperature was reached, the gas was switched from nitrogen to air and the reactor was sparged with air at 250 cc/minute. Samples were taken and analyzed by gas chromatography. At the end of the reaction, the gas was switched back to nitrogen and the heat was turned off.

Figure 2:
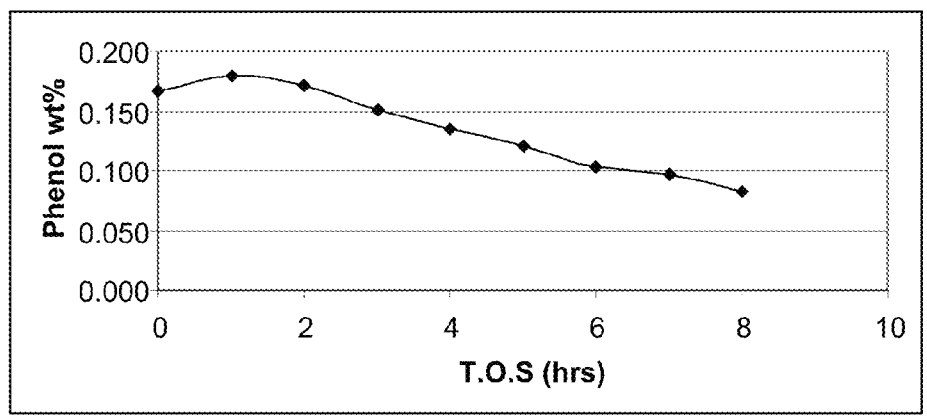
FIG. 2 is a graph of phenol content against time on stream for the oxidation of cyclohexylbenzene in the presence of 0.167 wt % phenol and N-hydroxyphthalimide (NHPI) according to Example 3.

The results of the processes described in Examples 1 to 3 are summarized in FIGS. 1 and 2. From FIG. 1 it will be seen that no oxidation was observed when phenol was added to the cyclohexylbenzene in the absence of NHPI. In the presence of NHPI, the addition of phenol decreased the oxidation rate as compared to the pure cyclohexylbenzene feed but did not completely inhibit the reaction. FIG. 2 shows that more than half of the phenol was converted during the reaction of Example 3 when NHPI was added to the CHB/phenol feed.

EXAMPLE 4

Oxidation of CHB Using NHPI as the Catalyst at 110° C.

150 g of cyclohexylbenzene from TCI America and 0.16 g NHPI from TCI were weighed into a Parr reactor fitted with a stirrer, thermocouple, gas inlet, sampling port and a condenser containing a Dean-Stark trap for water removal. The reactor contents were stirred at 1000 rpm and sparged with nitrogen at a flow rate of 250 cc/minute for 5 minutes. The reactor, while maintained under a nitrogen sparge, was then heated to 110° C. When the reaction temperature was reached, the gas was switched from nitrogen to air and the reactor was sparged with air at 250 cc/minute. Samples were taken and analyzed by gas chromatography. At the end of the reaction, the gas was switched back to nitrogen and the heat was turned off.

Figure 3:
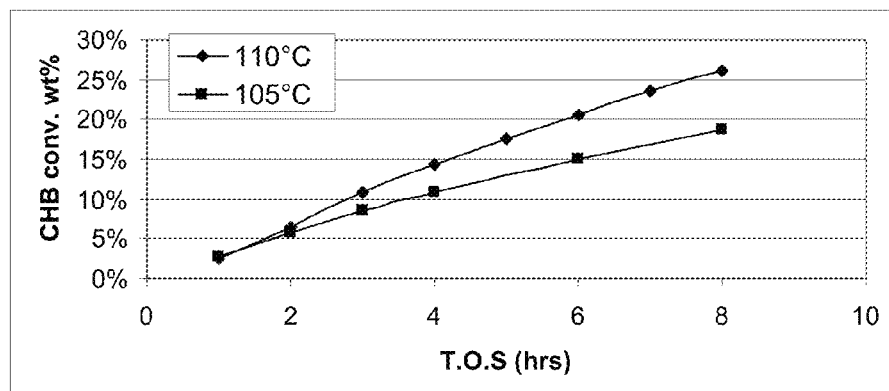
FIG. 3 is a graph comparing the cyclohexylbenzene conversion against time on stream for the oxidation of cyclohexylbenzene at 105° C. in the presence of N-hydroxyphthalimide (NHPI) according to Example 1 and the oxidation of cyclohexylbenzene at 110° C. in the presence of N-hydroxyphthalimide (NHPI) according to Example 4.
Figure 4:
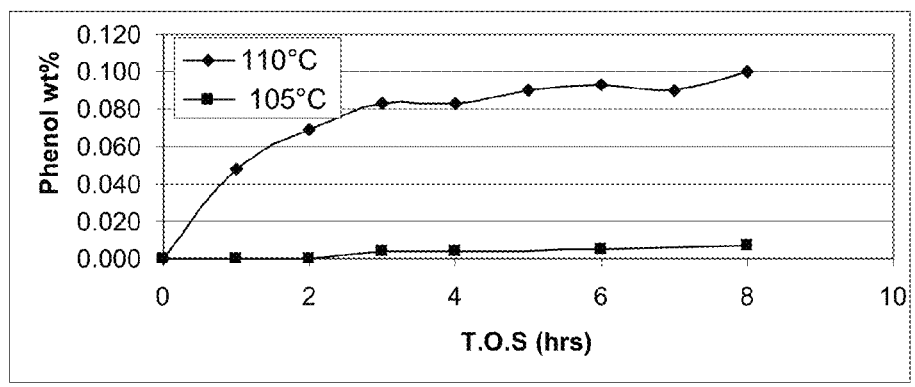
FIG. 4 is a graph comparing the phenol content against time on stream for the oxidation of cyclohexylbenzene at 105° C. in the presence of N-hydroxyphthalimide (NHPI) according to Example 1 and the oxidation of cyclohexylbenzene at 110° C. in the presence of N-hydroxyphthalimide (NHPI) according to Example 4.

FIGS. 3 and 4 show respectively the cyclohexylbenzene conversion and the phenol production against time on stream for the NPHI catalyzed processes of Examples 1 and 4. FIG. 4 indicates that although around 1000 ppm phenol was formed during the process of Example 4, the NHPI maintained a high oxidation reaction rate.

EXAMPLE 5

Oxidation of CHB in the Presence of 0.167 wt % Phenol and NHPI Catalyst 150 g of cyclohexylbenzene and 0.16 g NHPI from TCI were weighed into a Parr reactor fitted with a stirrer, thermocouple, gas inlet, sampling port and a condenser containing a Dean-Stark trap for water removal. The reactor contents were stirred at 1000 rpm and sparged with nitrogen at a flow rate of 250 cc/minute for 5 minutes. The reactor, while maintained under a nitrogen sparge, was then heated to 105° C. When the reaction temperature was reached, the gas was switched from nitrogen to air and the reactor was sparged with air at 250 cc/minute. Samples were taken and analyzed by gas chromatography. After five hours on stream, 0.2505 g phenol from TCI America was added to the composition and the reaction was continued for another two hours. At the end of the reaction, the gas was switched back to nitrogen and the heat was turned off.

Figure 5:
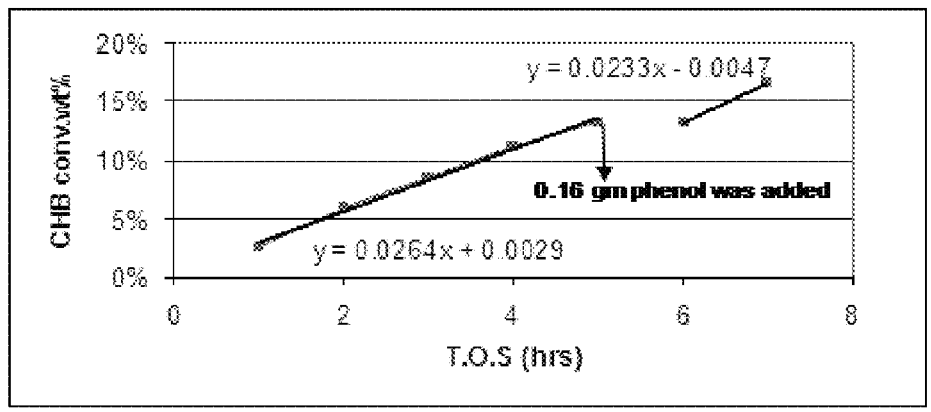
FIG. 5 is a graph of cyclohexylbenzene conversion against time on stream for the oxidation of cyclohexylbenzene according to Example 5.

The results of Example 5 are plotted in FIG. 5 and show that, although addition of phenol initially terminated the oxidation reaction, after an hour a similar reaction rate to that before the phenol addition was observed, indicating that NHPI was maintaining a similar reaction rate even at the higher phenol level.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Additionally or alternatively, the invention can be described by the following embodiments:

1. A process for oxidizing an alkylbenzene, the process comprising:

(a) supplying a composition comprising (i) an alkylbenzene of the general formula (I):

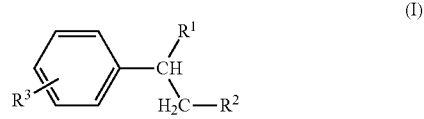

(I)

where $R^1$ and $R^2$ each independently represents hydrogen or an alkyl group having from 1 to 4 carbon atoms, wherein $R^1$ and $R^2$ may be joined to form a cyclic group having from 4 to 10 carbon atoms, the cyclic group being optionally substituted, and $R^3$ represents hydrogen, one or more alkyl groups having from 1 to 4 carbon atoms or a cyclohexyl group; and (ii) about 0.05 wt % to about 5.0 wt % of phenol, the wt % based upon total weight of the composition; and (b) contacting the composition with oxygen in the presence of a catalyst containing a cyclic imide having the general formula (II):

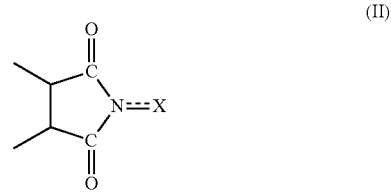

(II)

wherein X represents an oxygen atom, a hydroxyl group, or an acyloxy group, and wherein the contacting step (b) is conducted under conditions effective to convert at least a portion of the alkylbenzene to an alkylbenzene hydroperoxide.

2. The process of embodiment 1 and further comprising:

(c) cleaving at least a portion of the alkylbenzene hydroperoxide produced by the contacting step (b) to produce phenol and cyclohexanone.

3. The process of embodiment 2, wherein at least a portion of the phenol present in the composition is provided from a recycle stream from the contacting step (b) and/or the cleaving step (c).

4. The process of embodiment 1, wherein the composition comprises from about 0.1 wt % to about 1 wt % of phenol based upon total weight of the composition.

5. The process of embodiment 1, wherein the composition comprises from about 0.15 wt % to about 0.5 wt % of phenol based upon total weight of the composition.

6. The process of embodiment 1, wherein the alkylbenzene is selected from cumene, sec-butylbenzene, cyclohexylbenzene, and mixtures thereof.

7. The process of embodiment 1, wherein the cyclic imide has the general formula (III):

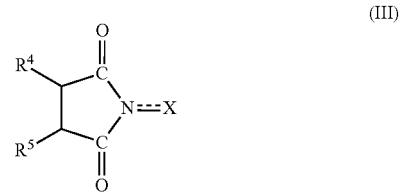

(III)

wherein X represents an oxygen atom, a hydroxyl group, or an acyloxy group and $R^4$ and $R^5$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^4$ and $R^5$ may be bound together to form a double bond or an aromatic- or non-aromatic ring.

8. The process of embodiment 1, wherein the cyclic imide comprises N-hydroxyphthalimide.

9. The process of embodiment 1, wherein the catalyst containing a cyclic imide having the general formula (II) is effective to remove at least a portion of the phenol.

10. The process of embodiment 1, wherein the cyclic imide is present in an amount of between 0.05 wt % and 5 wt % of the composition.

11. The process of embodiment 1, wherein the contacting step (b) is conducted at a temperature of between 90° C. and 150° C.

12. The process of embodiment 1, wherein the contacting step (b) is conducted at a temperature of between 105° C. and 120° C.

13. The process of embodiment 1, wherein the contacting step (b) is conducted at a pressure between 15 kPa and 500 kPa.

14. At least one of phenol and cyclohexanone produced by the process of embodiment 2.

15. The process of embodiment 2, wherein at least a portion of the phenol produced in the cleaving step (c) is converted to one or more of a phenolic resin, bisphenol A, ε-caprolactam, an adipic acid, or a plasticizer.

16. The process of embodiment 2, wherein at least a portion of the cyclohexanone produced in the cleaving step (c) is converted into one or more of adipic acid, a cyclohexanone resin, a cyclohexanone oxime, caprolactam, or nylon.

17. The process of embodiment 1, wherein the composition comprises at least 5 wt % of the alkylbenzene, the wt % based upon total weight of the composition.

18. A process for producing phenol and/or cyclohexanone, the process comprising:

(a) contacting benzene and hydrogen under hydroalkylation conditions to produce cyclohexylbenzene;

(b) supplying a feed comprising (i) at least a portion of the cyclohexylbenzene from the contacting step (a) and 0.05 wt % to 5 wt % of phenol based upon total weight of the feed to at least one oxidation reaction zone;

(c) contacting the feed in the at least one oxidation reaction zone with an oxygen-containing gas in the presence of a catalyst containing a cyclic imide having the general formula (II)

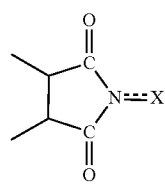

wherein X represents an oxygen atom, a hydroxyl group, or an acyloxy group and wherein the contacting step (c) is conducted under conditions effective to convert at least a portion of the cyclohexylbenzene to cyclohexylbenzene hydroperoxide and produce an oxidation effluent stream comprising cyclohexylbenzene hydroperoxide and unreacted cyclohexylbenzene;

(d) cleaving at least a portion of the cyclohexylbenzene hydroperoxide in at least one cleavage reaction zone to produce a cleavage effluent stream comprising phenol, cyclohexanone and unreacted cyclohexylbenzene; and (e) providing a recycle stream comprising unreacted cyclohexylbenzene and at least 0.05 wt % phenol from the oxidation effluent stream and/or the cleavage effluent stream to the at least one oxidation reaction zone.

19. The process of embodiment 18, wherein the feed comprises from 0.1 wt % to 1 wt % of phenol based upon total weight of the feed.

20. The process of embodiment 18, wherein the feed comprises from 0.15 wt % to 0.5 wt % of phenol based upon total weight of the feed.

21. The process of embodiment 18, wherein the cyclic imide has the general formula (III):

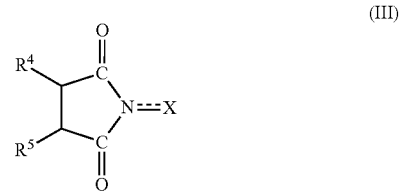

wherein X represents an oxygen atom, a hydroxyl group, or an acyloxy group and $R^4$ and $R^5$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^4$ and $R^5$ may be bound together to form a double bond or an aromatic- or non-aromatic ring.

22. The process of embodiment 18, wherein the cyclic imide comprises N-hydroxyphthalimide.

23. The process of embodiment 18, wherein the cyclic imide is added to the at least one oxidation reaction zone in an amount between 0.05 wt % and 5 wt % of the feed.

24. A process for producing phenol and cyclohexanone, the process comprising:

(a) contacting benzene and hydrogen under hydroalkylation conditions to produce cyclohexylbenzene;

(b) supplying a feed comprising (i) at least a portion of the cyclohexylbenzene from the contacting step (a) and 0.05 wt % to 5 wt % of phenol based upon total weight of the feed to at least one oxidation reaction zone;

(c) contacting the feed in the at least one oxidation reaction zone with N-hydroxyphthalimide under conditions effective to convert at least a portion of the cyclohexylbenzene to cyclohexylbenzene hydroperoxide and produce an oxidation effluent stream comprising cyclohexylbenzene hydroperoxide and unreacted cyclohexylbenzene;

(d) cleaving at least a portion of the cyclohexylbenzene hydroperoxide in at least one cleavage reaction zone to produce a cleavage effluent stream comprising phenol, cyclohexanone and unreacted cyclohexylbenzene;

wherein at least a portion of the phenol in the feed is supplied from a recycle stream comprising unreacted cyclohexylbenzene and phenol from the oxidation effluent stream and/or the cleavage effluent stream, and wherein the N-hydroxyphthalimide is effective to remove at least a portion of the phenol from the feed in the oxidation reaction zone.

The invention claimed is:

1. A process for oxidizing an alkylbenzene, the process comprising:

(a) supplying a composition comprising (i) an alkylbenzene of the general formula (I):

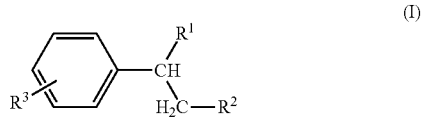

where $R^1$ and $R^2$ each independently represents hydrogen or an alkyl group having from 1 to 4 carbon atoms, wherein $R^1$ and $R^2$ may be joined to form a cyclic group having from 4 to 10 carbon atoms, the cyclic group being optionally substituted, and $R^3$ represents hydrogen, one or more alkyl groups having from 1 to 4 carbon atoms or a cyclohexyl group and (ii) about 0.05 wt % to about 5.0 wt % of phenol, the wt % based upon total weight of the composition; and (b) contacting the composition with oxygen in the presence of a catalyst containing a cyclic imide having the general formula (III):

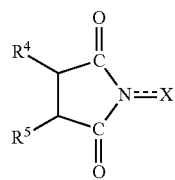

(III)

wherein X represents an oxygen atom, a hydroxyl group, or an acyloxy group, and $R^4$ and $R^5$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^4$ and $R^5$ may be bound together to form a double bond or an aromatic- or non-aromatic ring, and wherein the contacting step (b) is conducted under conditions effective to convert at least a portion of the alkylbenzene to an alkylbenzene hydroperoxide.

2. The process of claim 1, and further comprising:
(c) cleaving at least a portion of the alkylbenzene hydroperoxide produced by the contacting step (b) to produce phenol and cyclohexanone.

3. The process of claim 2, wherein at least a portion of the phenol present in the feed in the composition is provided from a recycle stream from the contacting step (b) and/or the cleaving step (c).

4. The process of claim 1, wherein the composition comprises from about 0.1 wt % to about 1 wt % of phenol based upon total weight of the composition.

5. The process of claim 1, wherein the composition comprises from about 0.15 wt % to about 0.5 wt % of phenol based upon total weight of the composition.

6. The process of claim 1, wherein the alkylbenzene is selected from cumene, sec-butylbenzene, cyclohexylbenzene and mixtures thereof.

7. The process of claim 1, wherein the cyclic imide has the general formula (II):

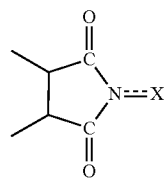

(II)

wherein X represents an oxygen atom, a hydroxyl group, or an acyloxy group.

8. The process of claim 1, wherein the cyclic imide comprises N-hydroxyphthalimide.

9. The process of claim 1, wherein the catalyst containing a cyclic imide having the general formula (II) is effective to remove at least a portion of the phenol.

10. The process of claim 1, wherein the cyclic imide is present in an amount of between 0.05 wt % and 5 wt % of the composition.

11. The process of claim 1, wherein the contacting step (b) is conducted at a temperature of between 90° C. and 150° C.

12. The process of claim 1, wherein the contacting step (b) is conducted at a temperature of between 105° C. and 120° C.

13. The process of claim 1, wherein the contacting step (b) is conducted at a pressure between 15 kPa and 500 kPa.

14. The process of claim 2, wherein at least a portion of the phenol produced in the cleaving step (c) is converted to one or more of a phenolic resin, bisphenol A, ε-caprolactam, an adipic acid, or a plasticizer.

15. The process of claim 2, wherein at least a portion of the cyclohexanone produced in the cleaving step (c) is converted into one or more of adipic acid, a cyclohexanone resin, a cyclohexanone oxime, caprolactam, or nylon.

16. The process of claim 1, wherein the composition comprises at least 5 wt % of the alkylbenzene, the wt % based upon total weight of the composition.

17. A process for producing phenol and/or cyclohexanone, the process comprising:
(a) contacting benzene and hydrogen under hydroalkylation conditions to produce cyclohexylbenzene;
(b) supplying a feed comprising (i) at least a portion of the cyclohexylbenzene from the contacting step (a) and 0.05 wt % to 5 wt % of phenol based upon total weight of the feed to at least one oxidation reaction zone;
(c) contacting the composition with oxygen in the presence of a catalyst containing a cyclic imide having the general formula (III):

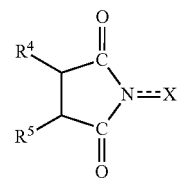

(III)

wherein X represents an oxygen atom, a hydroxyl group, or an acyloxy group, and $R^4$ and $R^5$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^4$ and $R^5$ may be bound together to form a double bond or an aromatic- or non-aromatic ring,
wherein the contacting step (c) is conducted under conditions effective to convert at least a portion of the cyclohexylbenzene to cyclohexylbenzene hydroperoxide and produce an oxidation effluent stream comprising cyclohexylbenzene hydroperoxide and unreacted cyclohexylbenzene;
(d) cleaving at least a portion of the cyclohexylbenzene hydroperoxide in at least one cleavage reaction zone to produce a cleavage effluent stream comprising phenol, cyclohexanone and unreacted cyclohexylbenzene; and
(e) providing a recycle stream comprising unreacted cyclohexylbenzene and at least 0.05 wt % phenol from the oxidation effluent stream and/or the cleavage effluent stream to the at least one oxidation reaction zone.

18. The process of claim 17, wherein the feed comprises from 0.1 wt % to 1 wt % of phenol based upon total weight of the feed.

19. The process of claim 17, wherein the feed comprises from 0.15 wt % to 0.5 wt % of phenol based upon total weight of the feed.

20. The process of claim 17, wherein the cyclic imide has the general formula (II):

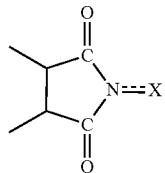

(II)

wherein X represents an oxygen atom, a hydroxyl group, or an acyloxy group.

21. The process of claim 1, wherein the cyclic imide comprises N-hydroxyphthalimide.

22. The process of claim 1, wherein the cyclic imide is added to the at least one oxidation reaction zone in an amount between 0.05 wt % and 5 wt % of the feed.

23. A process for producing phenol and cyclohexanone, the process comprising:
(a) contacting benzene and hydrogen under hydroalkylation conditions to produce cyclohexylbenzene;
(b) supplying a feed comprising (i) at least a portion of the cyclohexylbenzene from the contacting step (a) and 0.05 wt % to 5 wt % of phenol based upon total weight of the feed to at least one oxidation reaction zone;
(c) contacting the feed in the at least one oxidation reaction zone with N-hydroxyphthalimide under conditions effective to convert at least a portion of the cyclohexylbenzene to cyclohexylbenzene hydroperoxide and produce an oxidation effluent stream comprising cyclohexylbenzene hydroperoxide and unreacted cyclohexylbenzene;
(d) cleaving at least a portion of the cyclohexylbenzene hydroperoxide in at least one cleavage reaction zone to produce a cleavage effluent stream comprising phenol, cyclohexanone and unreacted cyclohexylbenzene;
wherein at least a portion of the phenol in the feed is supplied from a recycle stream comprising unreacted cyclohexylbenzene and phenol from the oxidation effluent stream and/or the cleavage effluent stream, and
wherein the N-hydroxyphthalimide is effective to remove at least a portion of the phenol from the feed in the oxidation reaction zone.

* * * * *